United States Patent [19]
Apple et al.

[11] Patent Number: 6,120,540
[45] Date of Patent: Sep. 19, 2000

[54] RADIO PROSTHESIS

[76] Inventors: Marc G. Apple, 1606 Sycamore Hills Dr., Fort Wayne, Ind. 46804; Melvin J. Apple, 2553 NW. 52 St., Boca Raton, Fla. 33496

[21] Appl. No.: 09/234,965

[22] Filed: Jan. 21, 1999

Related U.S. Application Data

[60] Provisional application No. 60/073,096, Jan. 21, 1998.

[51] Int. Cl.$^7$ ........................................... A61F 2/02
[52] U.S. Cl. .................... 623/11.11; 623/18.11; 623/22.11; 623/23.11
[58] Field of Search ................... 623/18, 16, 17, 623/19, 20, 21, 22, 23, 22.11, 17.12, 11.11, 16.11, 18.11, 23.11

[56] References Cited

U.S. PATENT DOCUMENTS

| | | | |
|---|---|---|---|
| 4,936,823 | 6/1990 | Colvin et al. | 600/7 |
| 5,133,757 | 7/1992 | Sioshansi et al. | 623/18 |
| 5,397,329 | 3/1995 | Allen | 606/73 |
| 5,503,614 | 4/1996 | Liprie | 600/7 |
| 5,681,289 | 10/1997 | Wilcox et al. | 623/22 |
| 5,833,593 | 11/1998 | Liprie | 600/3 |
| 5,857,956 | 1/1999 | Liprie | 600/7 |
| 5,871,436 | 2/1999 | Eury | 600/3 |
| 5,906,573 | 5/1999 | Aretz | 600/3 |
| 5,919,126 | 7/1999 | Armini | 600/3 |

*Primary Examiner*—Jeffrey A. Smith
*Assistant Examiner*—Eduardo C. Robert

[57] ABSTRACT

An implant system and a method for delivering a dosage of radiation to targeted tissue. The system comprises a prosthetic device that functionally replaces or is additive to a body structure or joint, and a radio source material. The radio source material is positioned either on or within the prosthetic device. The actual radiation delivery distribution field has a similar configuration to the profile of the targeted tissue. The implant system is particularly useful for inhibiting heterotopic ossification.

20 Claims, 3 Drawing Sheets

RADIO PROSTHESIS

This application is a provision of Ser. No. 60/073,096, filed Jan. 21, 1998.

An implanted apparatus that is additive or a replacement to an anatomic body structure or joint for the purpose of delivering a pre-calibrated radiation doses to adjacent tissue to inhibit growth or migration of benign or malignant living cells to inhibit heterotopic ossification.

BACKGROUND OF THE INVENTION

Total prosthetic replacements of the human hip, knee and shoulder are now common orthopedic surgical procedures. As the age of the general population increases, the frequency for such replacements will increase. Symptoms generally include progressive degenerative osteoarthritis, prior localized trauma, previous local surgical procedures within the region, ankylosing spondylitis, and idiopathic skeletal hyperostosis.

A common delayed complication following such replacements is the development of heterotopic ossification within or about the immediate adjacent soft tissue and the prosthesis between the adjoining bone tissue. This complication results from excessive migration, replication, or differentiation of local primitive mesenchymal cells which are stimulated by the surgical trauma. These cells undergo subsequent metabolic and cytologic metamorphosis to become more specialized osteoblastic cells. These osteoblastic cells then produce osteoid which is eventually transformed into calcified deposits or bone tissue, but in undesirable locations.

Heterotopic ossification causes varying degrees of debilitating pain, functional or mobile impairment, and increases the likelihood of repeat procedures after a period of from several months to a few years. For all patients undergoing total prosthetic hip replacement, between 30 and 35 percent of all untreated patients develop some degree of functional impairment or progressive discomfort.

External beam irradiation has established therapeutic effectiveness. When such therapy is delivered within a narrow period of time, the prophylactic use of external beam radiation therapy has been shown to effectively reduce the incidence and severity of heterotopic ossification. A limited, relatively low-dose of focal ionizing radiation to the specific target tissue, when administered predominantly in the first several hours to two days after surgery has proven beneficial clinical results with virtually no short or long term side effects.

However, external beam radiation therapy is often not prescribed because of the time required for set-up and treatment, the availability of single fraction treatments and variations in prescribed dose, patient discomfort and side effects, the need to irradiate tissue outside the target field, and economic considerations. In addition, many patients are not considered for radiation treatment until late in the recovery process, which further limits treatment options.

What is needed is a process and structure for providing the radiation dose originating from an internal site to the targeted tissue, whereby the emission profile more closely matches the physical parameters profile of the targeted tissue than in conventional methods.

What is needed is a process and a structure that will eliminate the need for separate post-operative treatment while dramatically reducing any occurrence of heterotopic ossification.

What is needed is a process and a structure that is can be readily adapted for any surgical bone tissue replacement or additive procedures.

What is needed is a process and a structure that is easy to administer, safe for the patient, and will effectively reduce the formation of heterotopic ossification resulting from such surgical procedures.

SUMMARY OF THE INVENTION

The radio prosthesis apparatus and method of the present invention for applications such as a total hip prosthesis, whereby a radiation delivery system induces the emission of specific radio nuclides enabling the anatomic configuration of the implant, the controlled placement position of one or more radio nuclides, and the selection of the type or composition of the radio source material to deliver a confined and targeted tissue deposition of ionizing radiation to a pre-calibrated dose rate, depth dose, and total delivered dose of prescribed radiation.

The radio prosthesis apparatus and method of the present invention offer numerous medical, safety and economic advantages over conventional radio therapy. The structure of this system dramatically improves the delivery of the radiation to the target as compared with the non-target tissue, inherently accommodating for individual patient differences in morphology. Improved radiation efficacy is achieved by delivering a continuous dose rate of radiation and by utilizing known physical characteristics of various radio nuclides; such as half-life, specific activity, specific concentration, and type of energy decay.

The artificially implanted apparatus is functionally replacing or additive to a normal anatomic body structure or joint. The apparatus is implanted, imbedded, or contained in a housing for strategically localized solid, liquid, gel-like, gaseous, or other intermediate phase radio-emitting substance or capable of inducing ionizing radiation, phosphorescence, luminescence, or fluorescence; whereby a precalibrated general or specific total dose, dose rate, or depth dose is delivered to adjacent target tissue to inhibit growth, migration, or differentiation of benign or malignant living cells, for example to inhibit heterotopic ossification.

Since the radiation only travels a short distance within the patient's soft tissue and essentially only through the targeted area, there is minimal radiation risk to medical personnel and healthy tissue within the patient. Such radiation begins its effective delivery immediately at the time of the procedure and over the immediate critical time frame for heterotopic ossification formation. The dosage eventually decays to a non-radioactive state thereby enabling healing and without functional impairment to the prosthesis. The patient is discharged after recovery and receives the equivalent radiation benefit of several fractionated external beam treatments without the time, inconvenience, discomfort, and expense of conventional radio therapy, while minimizing exposure to nontargeted tissue. Also, the system and method of the present invention promote more routine use of prophylactic radiation to prevent heterotopic ossification.

For a more complete understanding of the radio prosthesis apparatus and method of the present invention, reference is made to the following detailed description and accompanying drawings in which the presently preferred embodiments of the invention are shown by way of example. As the invention may be embodied in many forms without departing from spirit of essential characteristics thereof, it is expressly understood that the drawings are for purposes of illustration and description only, and are not intended as a definition of the limits of the invention. Throughout the description, like reference numbers refer to the same component throughout the several views.

DETAILED DESCRIPTION OF THE PREFERRED EMBODIMENTS

The radio prosthesis apparatus and method of the present invention is useful in applications involving the replacement or addition of bone tissue. The radiation delivery system induces the emission of specific radio nuclides enabling the anatomic configuration of the implant, the controlled placement position of one or more radio nuclides, and the selection of the type or composition of the radio source material to deliver a confined and targeted tissue deposition of ionizing radiation to a pre-calibrated dose rate, depth dose, and total delivered dose of prescribed radiation.

While radio prothesis as discussed herein is directed to applications involving hip replacements for purposes of illustration only, it is readily understood by those skilled in the art that the principles of the present invention are applicable to other bone replacement medical applications such as knee, shoulder, foot and hand, a limb, the jaw or face, a tooth, and the like. The system and method of the present invention may also be applied to other implant replacement or additive sites where heterotopic ossification is a problem.

There are various design structures and ways of incorporation the radio substance with a prosthetic apparatus, as well as, methods of delivering the radioisotope materials as are hereinafter described.

Figure 1:
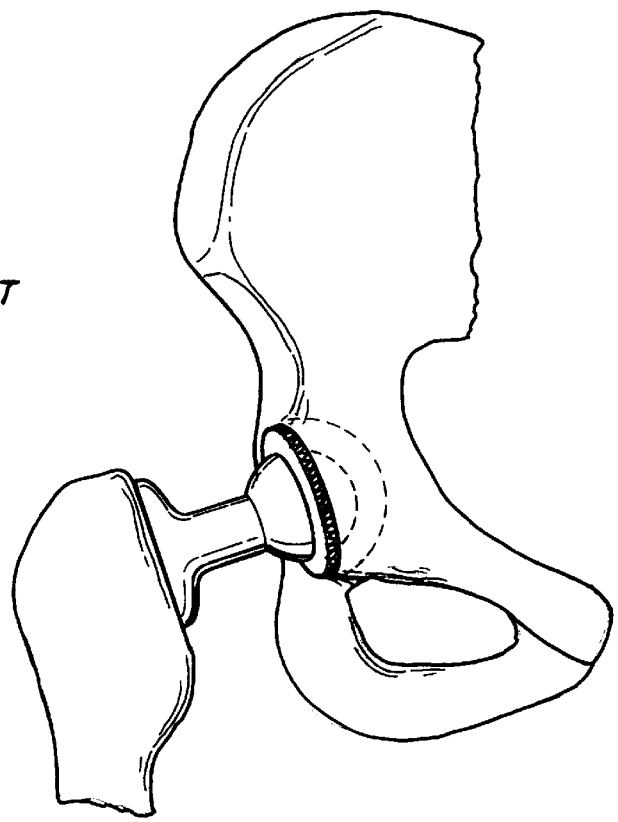
FIG. 1 is an environmental view of a hip replacement prosthesis device.
Figure 2:
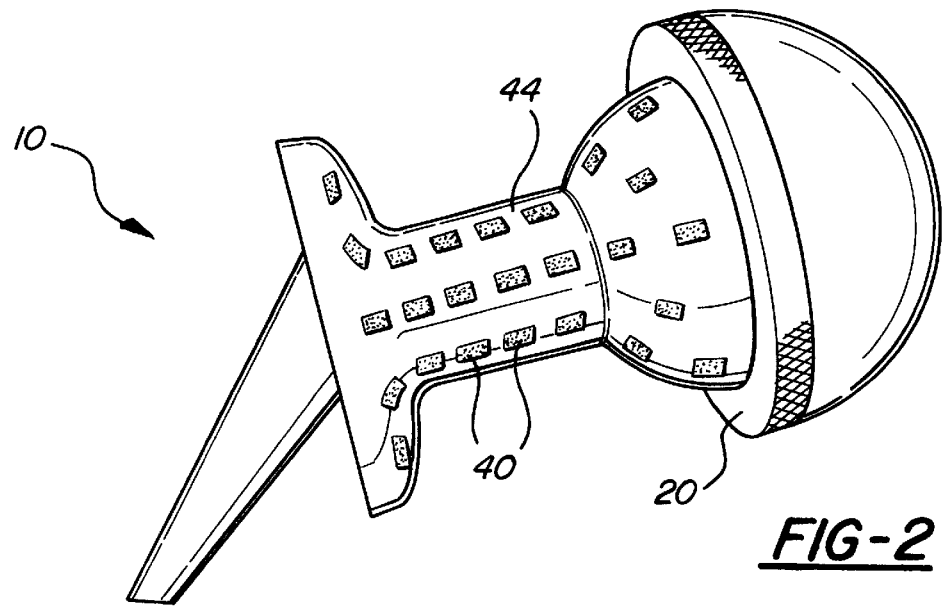
FIG. 2 is an exploded detail view of a first embodiment of the radio prothesis apparatus of the present invention.

FIG. 2 discloses a first preferred embodiment of the implant device [10], comprising a prosthetic device [20] and a radio source material [40] having radio nuclide impregnated modules [42] evenly spaced about the outer surface [44] thereof. The modules [42] are radioactive at the time of implantation having a shielded covering, and the coverings are removed prior to closure. The coverings are preferably malleable, attenuating, and readily removable. The modules [42] can also be inserted separately as a stored component and secured to the prosthetic device just prior to implant. The sizes, shapes, spacings, and emission activity levels of the modules [42] are morphometrically made to provide the desired isodose distribution based upon the physical properties of the radio nuclide. FIG. 1 discloses a prosthetic hip replacement device without the radio source material.

Figure 3:
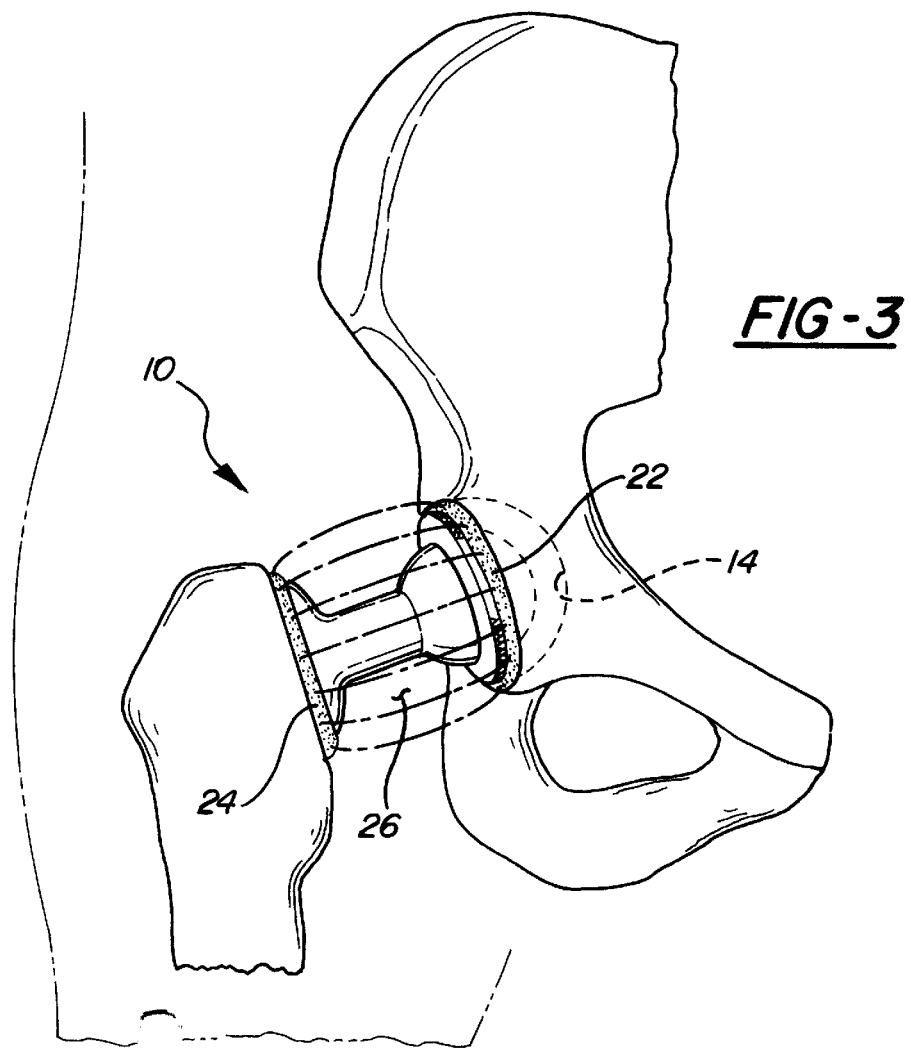
FIG. 3 is an environmental view of a first embodiment of the radio prothesis apparatus of FIG. 2, showing the shielded portions of the implant and the radio distribution field.

FIG. 3 shows the portions of bone tissue that are to be shielded from radiation exposure once the prosthesis hip replacement device [10] is implanted. The bone tissue of the hip socket [14] adjacent the device [10] is protected by a first shield [22] to minimize any radiation dose to the growth component of repair tissue. The bone tissue of the femur adjacent the device is protected by a second shield [24] to minimize radiation exposure to migratory growth cells along the inner portions of the prosthetic device. The radiation delivery field is ellipsoidal in shape and is positioned in the soft tissue [26] adjacent the device [10] between the shields [22 and 24].

Figure 4:
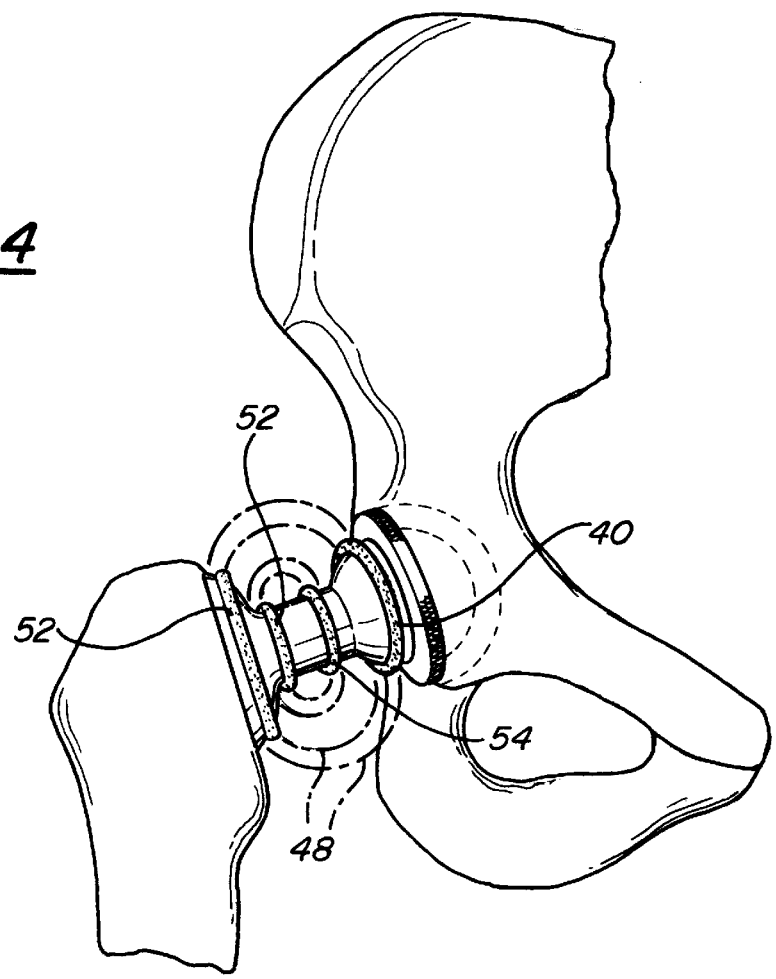
FIG. 4 is an environmental view of a second embodiment of the radio prothesis apparatus of the present invention having an ideal radiation delivery distribution through the targeted soft tissue.

FIG. 4 shows the ideal radiation delivery distribution through the targeted soft tissue. A plurality of spheres [48] is generated outwardly from the prosthetic device. Permanent or attachable thin rings [52] of radio source material, specifically sized so that the implant device provides three-dimensional tissue depth dose, dose rate, and total dose of radiation. The ring configuration does not interfere with the mobility of the implant. The radiation decay rate and limited travel range disintegrate after a period of several hours to several days. The radio source material [40] is circumferentially integrated into attachable and fitted annular strips [54].

Figure 6:
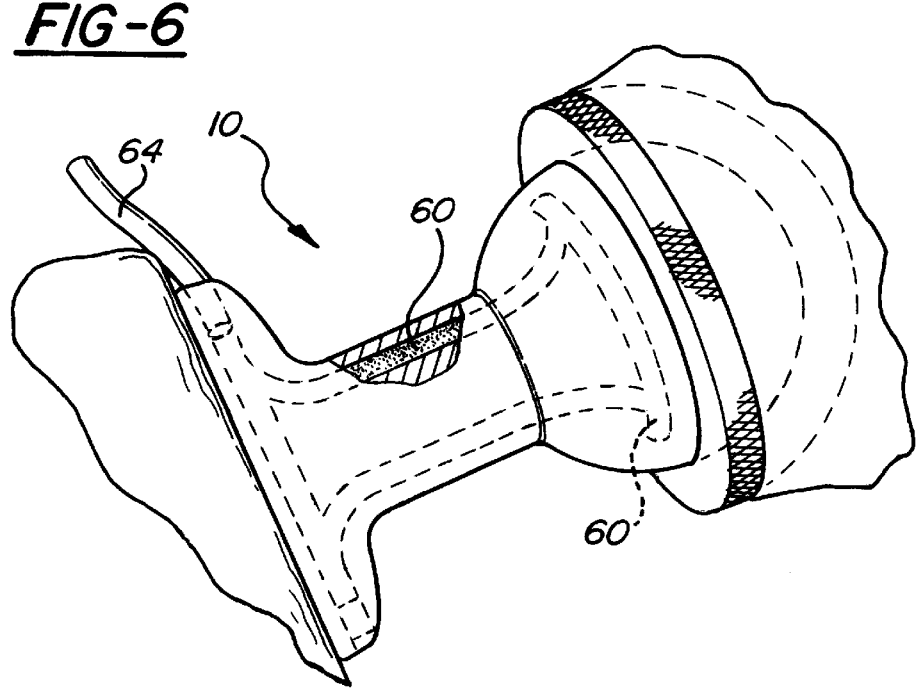
FIG. 6 is an exploded detail view of a third embodiment of the radio prothesis apparatus of the present invention having a series of interconnecting channels for the circulation of a radio source fluid or gel.
Figure 5:
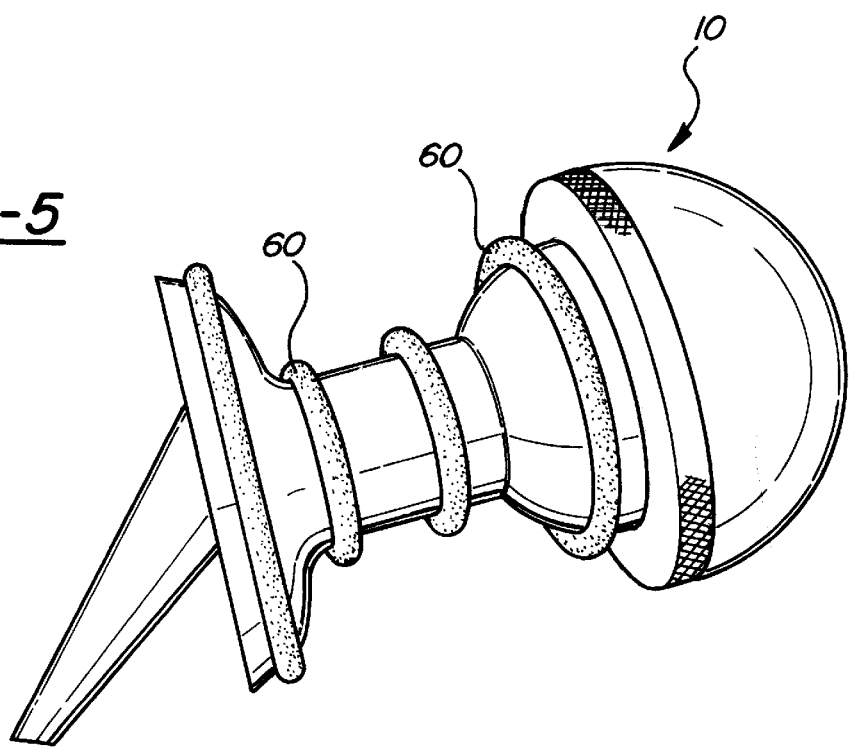
FIG. 5 is an exploded detail view of the second embodiment of the radio prothesis apparatus of FIG. 4.

FIGS. 5 and 6 disclose a third preferred embodiment of the implant system [10] of the present invention. The prosthetic device includes a series of interconnecting channels [60] for circulating a radio source fluid. The radio source fluid is injected after the wound closure through a leak-proof injection port [64] or is injected prior to wound closure. The injection port [64] is self sealing and readily removable once used. The radio fluid is either a gas, a liquid, or a gel and serves to distribute evenly along the thin radio penetrable channels [60] to provide even distribution of the radio-emissions to surrounding soft tissue.

The therapeutic radiation component is embedded into the prosthetic device prior to in vivo placement; placed in specific sections immediately prior to surgical implantation, placed after satisfactory implantation but prior to wound closure, or injected or cannulated after surgical closure, particularly, if a liquid, gel, or gas is the radio source material.

Gels, liquids, gases, or other inter-phase radio compounds can be loaded, injected, molded, screwed, foamed, mixed, taped or by other attachment methods and devices either directly or as a preformed radio-contained or measured unit onto or within a separate leading module specific for the prosthesis device or directly to the prosthetic apparatus, either before, during or after surgical implantation, without the need of an intermediary loading device.

Although this dose range of radiation has been safely used for heterotopic ossification and other non-malignant type of disease processes with a negligible risk of delayed tumor formation or tissue necrosis, the prosthesis and femoral head are not exposed to more than a minimal amount of radiation. These are specific sites of desired growth and repair cell migration thereby allowing for stable, permanent integration of the fixed components of the prosthesis into prepped bone. Patients require formal fluoroscopic simulation and dosimetry planning with defined fields for delivery of external beam radiotherapy.

Total doses of less than 700 cGy begin to show diminished efficacy versus compromise for any patient comfort or radiation risks. Accordingly, a dose range of 700 to 900 cGy is able to maintain heterotopic ossification formation rates of clinical significance to between 1 and 9 percent.

The radio nuclide component may be any humanly compatible and therapeutically applicable solid, liquid, gas, gel, or other intermediate phase radio nuclide or radioisotope compounds which emit gamma rays, x-rays, beta particles, alpha particles, positrons, auger electrons, photons, or any combination thereof produced by nuclear decay; isomeric transition; electron capture; fluorescent, phosphorescent or luminescent induction; external bombardment activation; electrical stimulation or any combination thereof.

Specific primary radio nuclides, either in stable or radioactive form include but are not limited to xenon, krypton, neon, argon, radon, technetium, rhenium, yttrium, phosphorus, iodine, strontium, samarium, gold, copper, palladium, iridium, tin, rubidium, osmium, platinum, ytterbium, cesium, americium, radium, thallium, chromium, vanadium, barium, titanium, bismuth, and rhodium. More particularly, the specific primary radio nuclides of choice are yttrium, strontium, iridium, iodine, palladium, and cesium.

The utilization and integration of any of these isotopes are applied to the device to enhance individual energy emissions and tissue penetration, in vivo safety, half-life decay properties and specific activities or concentrations of materials. A near ideal effect on the target tissue and depth is thereby achieved with regard to dose rate, depth dose, total does, and elimination rates. The preferred dose rates deliver energy in the range of 50 to 250 cGy/hr. Acceptable dose rates also include from 10 to below 50 cGy/hr and above 250 to 500 cGy/hr. Dose rates in the order of magnitude of from 10 to 200 cGy/min may be of benefit, if the half-life and millicuries of radioactivity can be short (several minutes) and low respectively or radio-material has a short dwell time and is removed. Dose rates per millicurie are between 0.5 cGy/min and 200 cGy/min mCi.

The total dose delivered to the targeted tissue are preferably between 700 cGy and 2000 cGy. Also, an acceptable total dose is from 200 to below 700 cGy, and above 2000 to 3500 cGy. The total dose to nontargeted soft tissue and bone tissue is preferably up to 500 cGy, and above 500 to 1500 is acceptable. The radio-dose prescription is precalibrated for each specific prosthesis size and application site and marked directly on the prosthesis apparatus. This would be intended to deliver a fixed dose and dose rate range.

Also, a sensor (not shown) may be used to monitor, verify, or control the delivery of the prescribed dose of radiation. Emergency release and retrieval elements enable the immediate removal of at least the radioactive component of the prosthesis.

Other sites of use for a radio-implant include all fixed or mobile joints, compartmental soft tissues and axial or appendicular bones.

Solid or gel-phase compounds may be pre-adhered to the prosthesis by processes involving laser techniques, chemical bonding, electro-ion exchange, thermal conditioning, emulsion-type technologies, or emulsion slip coatings. Ion beam bombardment or deposition to reduce adhesions, thrombus, and provide anti-microbial properties may be applied and is now commercially available from Spire Corp, Bedford, Mass.

Similar methods may be applied to place radio source materials in customized and fitted loading compartments or modules which are attachable at specific sites on the prosthesis and can be placed prior to, during, or after surgical implantation of the prosthetic device.

In addition, a prefabricated, individualized unit dose of radio source material may be constructed in generic or customized form similar to a seed, wire, ball, plaque, powder, pellet, etc. or the like and thereby loaded, with then known specific quantities of radiation upon or within previously described attachable modules, units, compartments and then placed onto or within the prosthetic device. Likewise, these pre-measured, precalibrated radio dose units may be placed directly onto or within the prosthetic apparatus utilizing specifically designed slots, compartments, clips, sections, etc. or the like whereby an intermediary module or loading apparatus is not necessarily required.

The placement of the radio materials may be permanent dwelling, temporary with extraction, or with the option of multiple delayed introductions or retrieval mechanisms.

Primary materials of the individualized radio-unit loading modules or compartments, and prosthetic radio components are made from almost any materials. The radio components preferably comprise plastics; natural or synthetic rubbers; metals; metal-alloys; bio-compatible molecular chain compounds; allogenic or heterogenic natural or synthetic dissoluble compounds when in vivo (natural human, animal, or plant by-product materials); viton rubber; polyurethane, polyethylene, polyimide, polyvinylchloride, polyamide, polytetra fluoroethylene, silicone.

Alternative therapy options for heterotopic ossification include use of non-steroidal anti-inflammatory drugs such as indomethacin, administered at various dosing schedules from 8 days to 6 weeks of treatment. While this method of drug therapy has shown some benefit, it is effective than >700 cGy of irradiation for clinically significant (Brooken class II–IV) heterotopic ossification. In addition, many patients experience gastrointestinal-intestinal bleeding or gastritis with this drug, requiring additional medications. Furthermore, routine compliance by all at risk patients may falter thereby leaving an unknown risk of eventual heterotopic ossification failure or severity. Both methods offer consideration for optimized, long term outcome.

It will be readily apparent to those skilled in the art that the implementation and mechanization of the system and method of the present invention can be varied considerably to improve operation without going beyond the bounds of the present invention. For example, a programmed dose can be applied and administered from an implant that is controlled from an external source, whereby the emission, the decay rate, the initiation, duration, intensity, direction is regulated. In addition, a similar-type device can be mounted on bone tissue and directed at adjacent tissue for treatment, thereby eliminating exposure of healthy tissue to the controlled dose.

It is evident that many alternatives, modifications, and variations of the radio prosthesis apparatus and method of the present invention will be apparent to those skilled in the art in light of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

What is claimed is:

1. An implant system for delivering a dosage of radiation to targeted tissue, the system comprising:

a prosthetic device for implantation and retention to natural bone tissue and adjacent to the targeted tissue; and a radio source material disposed relative to the prosthetic device, the radio source material being part of the prosthetic device that is implanted, the radio source material being a non-chemical agent, any dispensation of the radio source material to the target tissue being minimal, the radio source material enabling radiation treatment to the targeted tissue, the radiation treatment being applied from the prosthetic device after implantation;

whereby a predetermined dosage of prescribed radiation to the targeted tissue is determined by using known physical characteristics of the radio source material and by controlling the placement of the radio source material relative to the targeted tissue.

2. The implant system of claim 1, wherein the radio source material is inserted during the implantation for the purpose of inhibiting complications caused by the implantation of the prosthetic device.

3. The implant system of claim 1, wherein the radio source material is inserted during the implantation for the purpose of preventing or treating heterotopic ossification.

4. The implant system of claim 1, further comprising a shield that protects nontargeted tissue from the radiation treatment.

5. The implant system of claim 1, wherein the radio source material is radio source fluid circulating within a plurality of interconnecting channels within the prosthetic device, the interconnecting channel being sealed once the radio fluid is disposed therein.

6. The implant system of claim 1, wherein the system minimizes the distribution of any radio source material into the targeted tissue.

7. A prosthetic device for delivering a dosage of radiation to targeted tissue, the prosthetic device having a function independent of radiation delivery, a radio source material being implanted with the prosthetic device, the implanted radio source material enabling a predetermined dosage of radiation treatment to be directed at the targeted tissue after implantation, the radio source material being designed to inhibit complications caused by the implantation of the prosthetic device, the dosage of prescribed radiation to the targeted tissue being predetermined by applying known physical characteristics of the radio source material and by controlling the placement of the radio source material relative to the targeted tissue.

8. The prosthetic device of claim 7, wherein the radio source material is prepackaged and secured to the prosthetic device that is implanted.

9. The prosthetic device of claim 7, wherein the radio source material is part of the prosthetic device that is implanted, the prosthetic device having a function independent of radiation delivery.

10. The prosthetic device of claim 7, wherein the radio source material is a nonchemical agent and the system avoids the distribution of radio source material into the targeted tissue.

11. A surgical method comprising:
introducing a prosthetic device including a radio source material, the prosthetic device and radio source material comprising a closed system for implantation within a patient, the prosthetic device having a function independent of radiation delivery, the radio source material being selected for delivering a predetermined dosage of the radiation from the radio source material to targeted tissue within a known profile, the profile of the targeted tissue being proximate to the implant site; and
implanting the prosthetic device into organic tissue during a surgical procedure, the radio source material in combination with the prosthetic device defining an actual radiation delivery distribution field, the actual radiation delivery distribution field having a similar configuration to the profile of the targeted tissue.

12. The surgical method of claim 11, further comprising applying the radiation treatment from the radio source material of the prosthetic device to the targeted tissue after implantation, the radio source material being a nonchemical agent and the system avoids the distribution of radio source material into the targeted tissue.

13. The surgical method of claim 11, further comprising selecting the radio source material having an emission profile that is generally the same as the targeted tissue.

14. An implant system for delivering a dosage of radiation to targeted tissue, the system comprising:
a prosthetic device for replacement of natural bone tissue and proximate to targeted tissue during a surgical procedure, the prosthetic device having a function independent of radiation delivery; and
a radio source material disposed about or within the prosthetic device, the radio source material being a non-chemical agent ant being selected for delivering a predetermined dosage of the radiation to the targeted tissue within a known profile, the known profile of the radio source material having an emission profile that is generally the same as the targeted tissue, the known profile being proximate to the implant site, the radio source material in combination with the prosthetic device defining an actual radiation delivery distribution field, the actual radiation delivery distribution field having a similar configuration to the known profile of the targeted tissue.

15. The implant system of claim 14, wherein the radio source material is for the purpose of preventing or treating of heterotopic ossification includes a radio nuclide selected from the group consisting of yttrium, strontium, iridium, iodine, palladium, and cesium, xenon, krypton, neon, argon, radon, technetium, rhenium, yttrium, phosphorus, iodine, strontium, samarium, gold, copper, palladium, iridium, tin, rubidium, osmium, platinum, Ytterbium, cesium, americium, radium, thallium, chromium, vanadium, barium, titanium, bismuth, and rhodium.

16. The implant system of claim 14, wherein the radio source material is a solid material disposed about the prosthetic device.

17. The implant system of claim 14, further comprising a shield that protects nontargeted tissue from the radiation treatment.

18. The implant system of claim 14, wherein the radio source material is part of the prosthetic device that is implanted, and any dispensation of the radio source material to the target tissue being minimal.

19. The implant system of claim 14, wherein the predetermined dosage of the radiation to the targeted tissue being between 10 to 500 cGy/hr.

20. A method for delivering prescribed radiation, the method comprising:
selecting a radio source material to deliver a confined and targeted tissue deposition of ionizing radiation for delivering a pre-calibrated dose rate, depth dose, and total delivered dose of prescribed radiation;
introducing a prosthetic device, the prosthetic device having a function independent of radiation delivery, the radio source material being selected to deliver the pre-calibrated dose rate, depth dose, and total delivered dose of prescribed radiation once implanted; and
delivering the pre-calibrated dose rate, depth dose, and total delivered dose of prescribed radiation to the targeted tissue after implantation;
whereby the radio source material is selected from the group consisting of yttrium, strontium, iridium, iodine, palladium, and cesium, xenon, krypton, neon, argon, radon, technetium, rhenium, yttrium, phosphorus, iodine, strontium, samarium, gold, copper, palladium, iridium, tin, rubidium, osmium, platinum, ytterbium, cesium, americium, radium, thallium, chromium, vanadium, barium, titanium, bismuth, and rhodium.

* * * * *